United States Patent [19]

Koutrouvelis

[11] Patent Number: 5,047,036

[45] Date of Patent: Sep. 10, 1991

[54] STEREOTACTIC DEVICE

[76] Inventor: Panos G. Koutrouvelis, 1201 Ballantrae La., McLean, Va. 22101

[21] Appl. No.: 437,605

[22] Filed: Nov. 17, 1989

[51] Int. Cl.⁵ .............................................. A61B 19/00
[52] U.S. Cl. ........................................ 606/130; 606/1
[58] Field of Search .............................. 128/395–398, 128/639, 751; 606/130, 1, 185; 378/162

[56] References Cited

U.S. PATENT DOCUMENTS

| 3,021,842 | 2/1962 | Flood . | |
|---|---|---|---|
| 3,955,558 | 5/1976 | Fuisz . | |
| 4,332,248 | 6/1982 | De Vitis . | |
| 4,350,159 | 9/1982 | Gouda . | |
| 4,638,799 | 1/1987 | Moore | 606/1 |
| 4,653,509 | 3/1987 | Oloff et al. | 128/751 |
| 4,733,661 | 3/1988 | Palestrant . | |
| 4,750,487 | 6/1988 | Zanetti | 606/185 |
| 4,841,967 | 6/1989 | Chang et al. | 606/185 |

Primary Examiner—C. Fred Rosenbaum
Assistant Examiner—William W. Lewis
Attorney, Agent, or Firm—Peter J. Georges

[57] ABSTRACT

A stereotactic device of simplified structure, adaptable to align and precisely orient a variety of medical devices such as differently sized needles, cannulas and guide wires into the human body for procedures such as tumor biopsies, percutaneous discectomies, cyst aspirations and tumor localizations is described. The device described is adapted for use in combination with a stereotactic bridge comprised of a span rotatable on its horizontal axis and movably affixed to a C.T. scan table or X-ray table by positioning means providing vertical and horizontal movement of the span. The described device is interactive with a C.T. scanner to achieve accurate placement of the oriented medical device. Use of the stereotactic bridge allows alignment of medical devices in sagittal orientation with a high degree of accuracy.

17 Claims, 4 Drawing Sheets

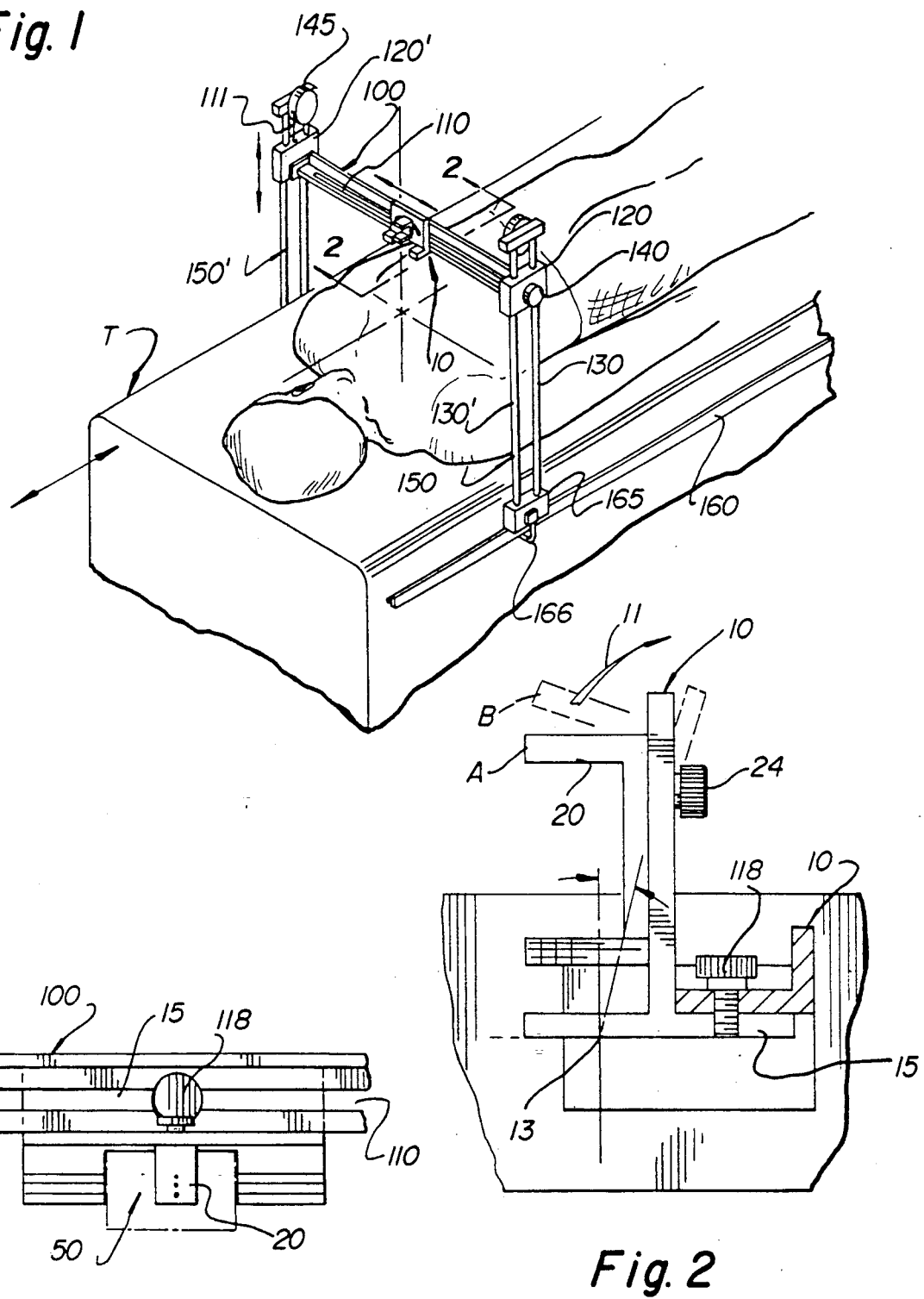

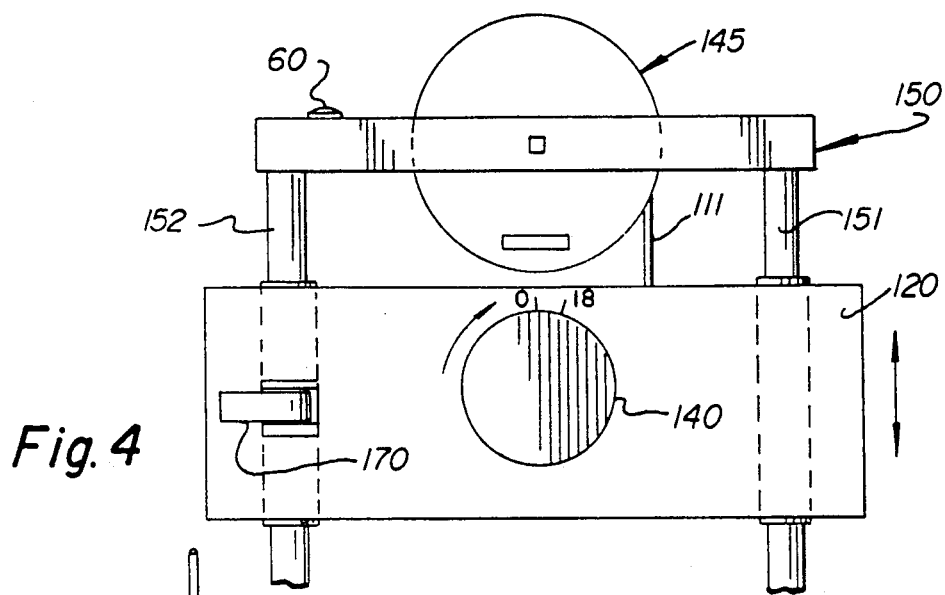
Fig. 4
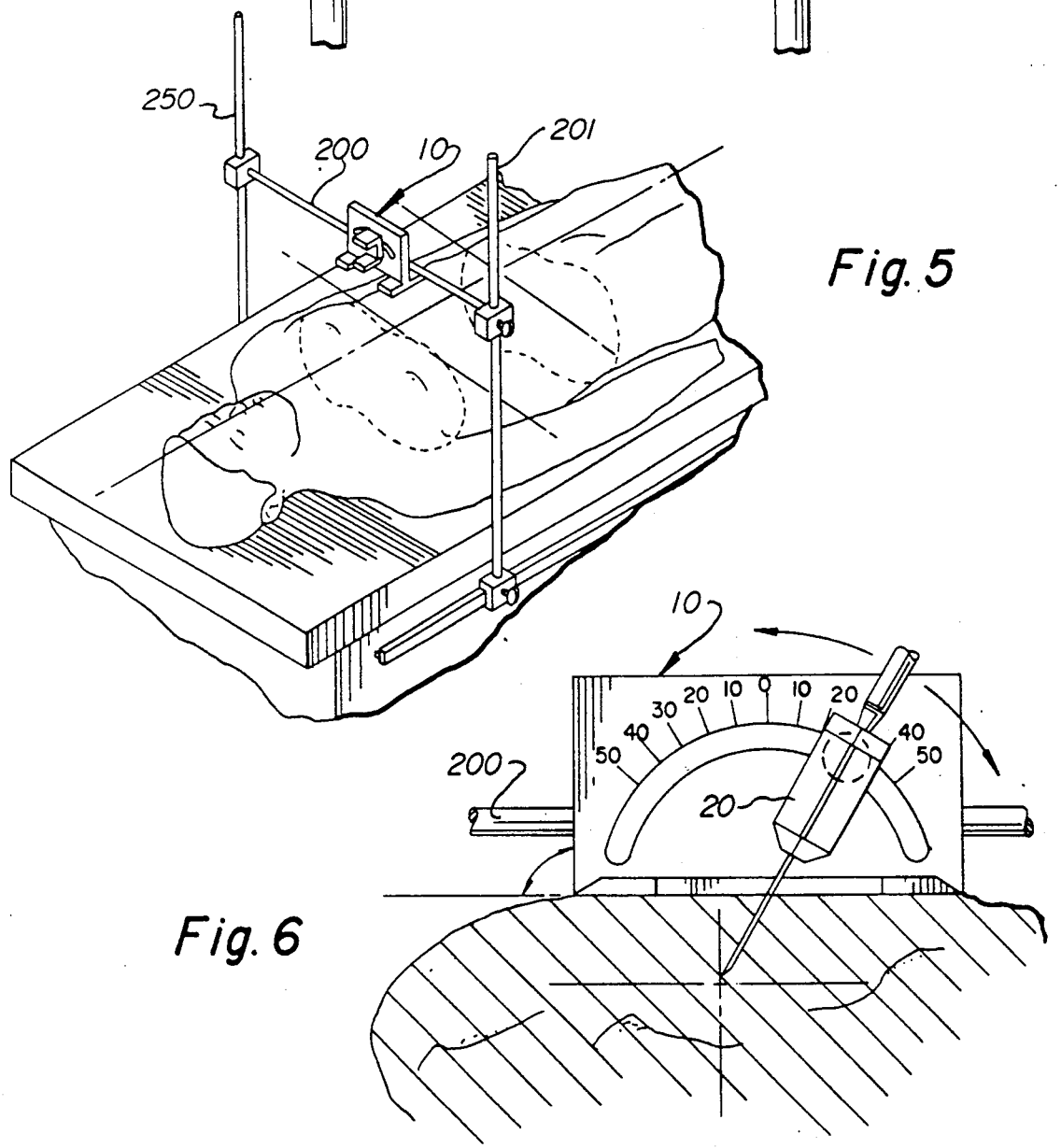
Fig. 5
Fig. 6

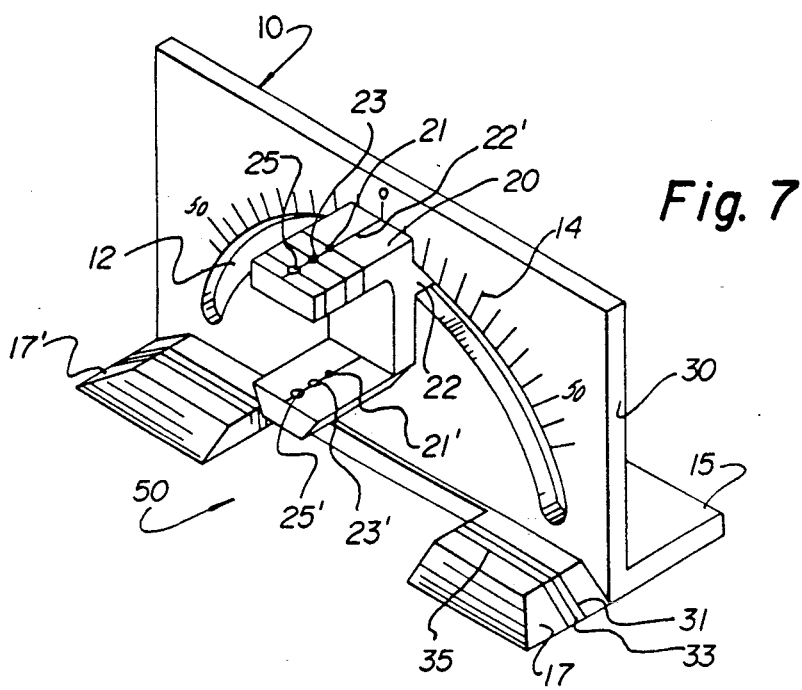
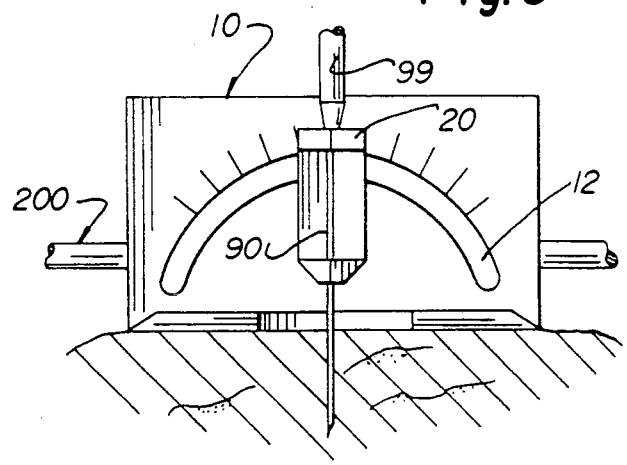
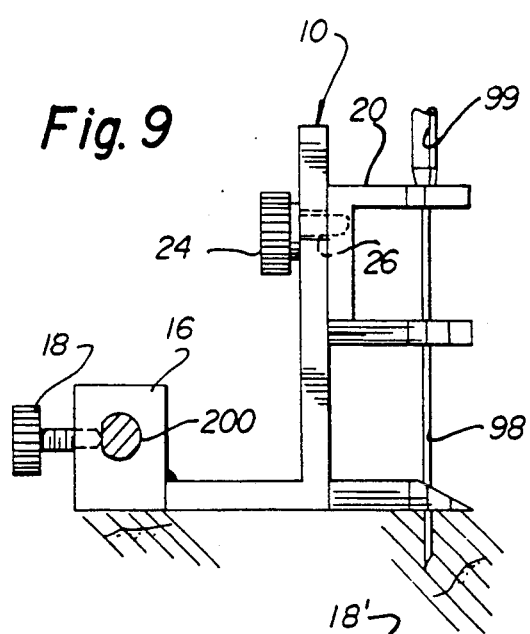
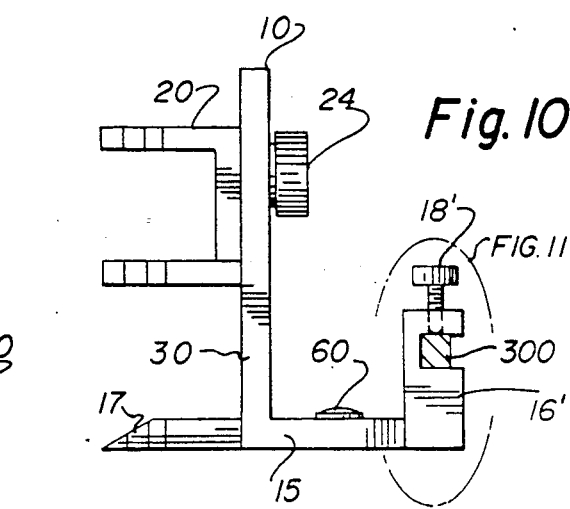
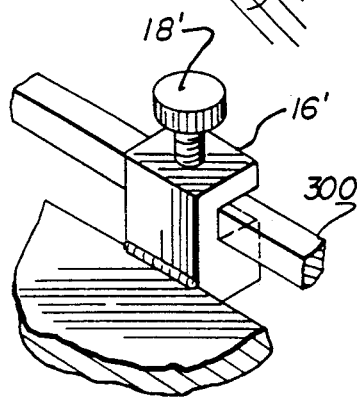

STEREOTACTIC DEVICE

BACKGROUND OF THE INVENTION

1. Field of the Invention

The present invention relates to a stereotactic device of simplified structure that is adaptable to align and precisely orient a variety of medical devices such as differently sized needles, cannulas and guide wires into the human body for procedures such as tumor biopsies, percutaneous discectomies, cyst aspirations and tumor localizations. The device of the present invention is adapted for use in combination with a stereotactic bridge comprised of a span rotatable on its horizontal axis and movably affixed to a C.T. scan table or X-ray table by positioning means. The positioning means allows vertical and horizontal movement of the span relative to said tables. The embodiment of the present invention relating to the combination of stereotactic device and bridge provides enhanced accuracy of placement and orientation of the medical device and avoids deviation during insertion attributable to hand movement. The device is interactive with a C.T. scanner to achieve accurate placement of the oriented medical device. The embodiment of the invention involving the use of the stereotactic bridge allows alignment of medical devices in sagittal orientation with a high degree of accuracy. Verification of positioning using the bridge can be accomplished in a facile manner.

2. Description of the Prior Art

The need for facilitating subcutaneous injections and orienting the insertion of cannulas or needles with precision in surgical procedures has given rise to the development of numerous devices adapted for such purposes.

An early device for facilitating subcutaneous injection is described in U.S. Pat. No. 3,021,842. A locking ball and socket arrangement is disclosed which is used for positioning a needle at a desired angle. To lock the ball in the socket at the preselected angle, the patentee provided a ball-engaging ring that was threaded on the socket.

More recently, after the advent of C.T. scanning, new devices for orienting and inserting cannulas or needles have been developed.

C.T. scanners are commonly used to provide doctors with cross-sectional internal pictures of a patient. Through the use of C.T. scanner technology, physicians are able to accurately place biopsy needles and drainage catheters into preselected areas of the body with a high degree of success.

C.T. scanners are capable of measuring a proposed trajectory for a biopsy needle or drainage catheter to within 0.1 millimeters with respect to depth, and within 0.1 degree with respect to angular orientation.

A hand-held needle guidance device which is suitable to accurately and easily use C.T. generated information to position a biopsy needle or drainage catheter relative to a patient's body is described in U.S. Pat. No. 4,733,661. The described guidance device utilizes a needle support arm hinged at the end of a planar base. The arm is oriented by protractor means also situated at the hinged end of the base. A wing nut arrangement is used to lock the pivoting arm at a predetermined angle relative to the planar base. The planar base is horizontally oriented by a circular bubble level on the base.

In apposition to the simple hand-held guidance device of U.S. Pat. No. 4,733,661, one finds in the art highly complex C.T. scanner guided stereotactic brain surgery devices utilizing skull mounted frames with associated complex positioning instruments. Such instruments, as pointed out in U.S. Pat. No. 4,733,661, are well-known in the art, such art being well referenced in U.S. Pat. No. 4,733,661.

A C.T. scanner guided stereotactic brain surgery instrument described in U.S. Pat. No. 4,350,159 is used to precisely insert an electrode in the brain of a patient for treatment of nervous disorders. The orientation of the inserted electrode at an angle to the plane formed by the frame is achieved utilizing a semicircular rotatable arc mounted on the frame onto which a movable electrode carrier can be locked. A separate protractor is used to orient the electrode carrier. For drilling the hole through which the electrode is inserted, the arc is rotated part of the way.

SUMMARY OF THE INVENTION

The present invention achieves movement of a medical device along an arc defined by an arcuate slot/opening in a protractor which operates as a means of both orienting and supporting a carrier which rides within the slot. The carrier can be locked into position along the arc defined by a slot at any preselected angle.

In accordance with the present invention, a T-shaped or L-shaped stereotactic device of simple structure allows a user to accurately introduce a medical device within a body at a preselected angle. The device is adapted for interactive use with a C.T. scanner and on a patient horizontally supported on the surface of a C.T. scan table. In one embodiment of the invention, the stereotactic device comprises a base having an upper surface exposed when the stereotactic device is in use and a lower surface placed on the body into which the medical device is to be introduced. The base has an opening therein, through which the part of the medical device to be placed within the body can pass unobstructed. The opening may be of any shape or size, provided that the instrument inserted into the patient can be accommodated. The opening defines the sterile field through which the medical device is inserted and therefore the size and placement should be appropriate for the use intended. In one embodiment of the invention, adapted to facilitate disengagement and removal of base and leg from the medical device, the opening in the base is formed by cutting out a portion of the base. Such opening is herein, alternatively, referred to as the cutout, cutout portion/opening or cephalic opening, the latter being a coined term referring to an opening in the base that begins at an edge of the base and is open toward the gantry of the C.T. scanner. This opening delimits the sterile field. The term "opening" includes the completely open side of the L-shaped device where the sterile field is delimited by the leg and base thereunder. By using a cutout as the opening, the stereotactic device can be removed by disengaging the carrier for the medical device and removing the stereotactic device away from the locus of insertion in a horizontal direction. A wall normal to the base, suitably the leg of a T-shaped aluminum bar, having an arcuate slot therein, defines a circular segment for angular orientation. The stereotactic device has a carrier for the medical device which is comprised of an arcuate portion which rides within the arcuate slot; retaining means for retaining the medical device in a fixed radial position relative to the arc defined by the arcuate slot and downwardly through the opening in the base; and, means for locking said carrier at a fixed position on the arcuate pathway formed by the slot.

There are markings on the wall along said arcuate slot for placement of the retaining means at a preselected point along said arcuate slot whereby the medical device retained thereby can be extended downwardly through the opening and into the body at a preselected angle. There are also markings on the surface and/or edges of said base for orientation of said base on the body.

Where linear markings are utilized to align the stereotactic device of the present invention, suitably one or more marks are scribed on the upper surface of the base and run along at least a portion of the length of the upper surface of the base in parallel with the wall. If extended across the base opening, the extended scribe mark/line would intersect the radial line defined by the pathway through which the medical device, e.g., a needle, is oriented. The linear scribe marks are particularly helpful in alignment of the stereotactic device where the base is made of a transparent material, e.g., a clear plastic such as one of the polycarbonates. Such plastics are among the materials which meet the structural requirements of the stereotactic device of the present invention and can withstand conditions of sterilization.

It has been found that alignment of the stereotactic device using markings on top of the base, can be facilitated if the edges of the base are beveled. Thus, the edges intersecting the plane formed by the transverse light source of the C.T. scanner are preferably beveled. In accordance with the embodiment of the invention involving beveling the edge of the base, the marking on the top of the base which is used to orient the stereotactic device, extends angularly within the plane of the image cross-section.

Accordingly, the alignment of the stereotactic device on the laser light beam reference line replicated on the patient can be readily confirmed by the physician by reference to the opposite marked ends. The markings at each end should fall on the reference line on the patient. Where a metallic base, suitably aluminum or some other nontransparent material, is used to fabricate the stereotactic device, beveling of the ends is much preferred, since alignment using the markings at the edges of the bases is facilitated where the mark can be placed adjacent to the reference line.

Where the retaining means is adapted to accommodate a series of differently sized devices, e.g., needles, a series of markings are suitably used, with one marking for orienting the pathway of each needle of varying size.

The center of the circle formed by extending the arcuate segment defined by the arcuate opening should be at a point in the plane formed by the bottom surface of the base.

A leveling means may be associated with the device to aid in orienting the longitudinal axis of the base horizontally. The leveling means suitably is a circular bubble level on the upper surface of the base. The site of the level is preferably situated on top of the horizontal base, on the side of the base extending outwardly from the surface of the leg facing away from the sterile field. The linear markings on the upper surface of said base suitably run along at least a portion of the length of the upper surface of the base in parallel with the surface of the leg. Preferably, the markings extend to the opposed edges of the base normal to the leg. Such edges are most preferably beveled to facilitate alignment of the stereotactic device using a reference line on the patient.

The present invention, as previously noted, is a guidance device for allowing a user to accurately introduce a medical device to a preselected point in a patient's body. The stereotactic device comprises a base including a plate to be placed on and/or supported by the patient's body and an upstanding leg positioned substantially perpendicular to the plate. The plate has an opening through which a lower part of the medical device can pass unobstructed into a predetermined part of the patient's body. The leg has an arcuate slot of a given width cut therethrough and is marked to indicate a preselected angle relative to the predetermined part of the patient's body which is accessible through the opening in the plate. A carrier, which rides within the arcuate slot cut through the leg of the base, carries a means for retaining the medical device in a fixed position relative to the riding means and a means for locking the retaining means at one of the preselected angles relative to the predetermined part of the patient's body. The riding means may be a cylindrical protrusion having a threaded bore therethrough and an outer diameter slightly less than the given width of the arcuate slot cut through the leg. Preferably, the retaining means is comprised of a pair of arms with threaded bores therethrough, spaced from each other at a distance less than the given length of the medical device to assure that said medical device can be held securely in the bores thereof. The locking means typically is comprised of a threaded fastener for engaging the threaded bore through the cylindrical protrusion of the riding means.

One aspect of the present invention comprises the use of the above-described stereotactic device in combination with a stereotactic bridge. The stereotactic bridge functions to both steady the stereotactic device and to assure alignment of the leg wall of the stereotactic device parallel to the plane described by the tomographic cut image.

The stereotactic bridge is adapted for affixation to patient tables typically used for positioning a patient in the gantry of a C.T. scanner or relative to an X-ray machine.

In one embodiment of the invention, stereotactic device placement is facilitated by using same in combination with a stereotactic bridge. The stereotactic bridge is comprised of stanchions and a span which overlies the patient. The span is used to support the stereotactic device. The span can be rotated axially, to orient the medical device carried along the arcuate track of the leg of the stereotactic device so that the part inserted into the patient is within the plane of the tomographic cut of the C.T. scanner. The tomographic cut image generated by the C.T. scanner is used to develop the locus of entry and angle of insertion of the medical device. The wall of the leg of the stereotactic device which carries the medical device must be in a plane parallel to the plane of the tomographic cut in order to ensure accurate placement of the medical device.

The stereotactic bridge is comprised of positioning means for positioning the stereotactic device relative to the patient.

The span of the stereotactic bridge is movable in a horizontal plane both towards and away from the gantry. Described in terms relative to the patient's torso, the horizontal movement is from head to foot, although the limits of horizontal movement need not traverse the entire length of the torso.

The means employed for horizontal movement may comprise a slide and guide arrangement along the side of the C.T. scan table. The horizontal guide, typically a metal rail, is parallel to the C.T. scan table surface and is affixed to the fixed support on which the movable table top of the C.T. scan table is carried. The patient is placed on the movable table top in the appropriate position for the medical procedure. The movable table top is used to move the patient into and away from the gantry of the C.T. scanner.

The bridge is movable in a vertical direction to rest the table on the patient's torso at the appropriate height.

The means employed for horizontal movement may comprise a slide and guide array of any configuration and suitably may be square, round or some other shape.

The stereotactic device which rides on the span and can be locked in position at a given point along the length of the span is thus movable side-to-side relative to the patient's torso.

The means employed for side-to-side movement may comprise a slide and guide array of any configuration, square, round or some other shape or any form of suitable track for movement for movement of the stereotactic device across the patient's body.

The sliding elements of the horizontal, vertical and side-to-side movement means suitably include means for securing the slides in the required positions. Locking means such as set screws, wing bolts, simple mechanical elements, can be used among others as slide/track locks. The stereotactic bridge architecture is chosen to achieve movement and positioning using simple and reliable mechanisms and the details of specific machine elements selected are such as would be appreciated by one skilled in the art.

In one specific embodiment of the present invention, the stereotactic device includes a guide attachment integral therewith that is comprised of a slide which rides on the span of the stereotactic bridge. Such side-to-side guide and slide arrangement provides the most elementary side-to-side positioning means for the stereotactic device carried by the bridge.

BRIEF DESCRIPTION OF THE DRAWINGS

FIG. 1 is a perspective of the embodiment of the invention involving in combination the stereotactic device and bridge.

FIG. 2 is a sectional view taken along 2—2 of FIG. 1.

FIG. 3 is a top view of FIG. 2.

FIG. 4 is a partial view of the top portion of the stanchion illustrating the negator spring and the rider on the stanchion rails including the nob which is used to adjust the sagittal angle and the camlock.

FIG. 5 illustrates a simplified and alternative embodiment of the combined stereotactic device and stereotactic bridge as illustrated in FIG. 8 (perspective view).

FIG. 6 is a front view of the device in use showing a partial cross-section of the torso to illustrate insertion of the needle to a fixed point.

FIG. 7 is a perspective view of a further embodiment of the stereotactic device illustrating the relationship of the needle holder and cutaway portion delimiting the sterile field.

FIG. 8 is a front view illustrating the front view of FIG. 7 with the needle in use being inserted vertically.

FIG. 9 is a side view of FIG. 8.

FIG. 10 is an end view illustrating an alternative embodiment using a rectangular span.

FIG. 11 is a partial section taken from FIG. 10.

DETAILED DESCRIPTION OF THE DRAWINGS

Figure 12:
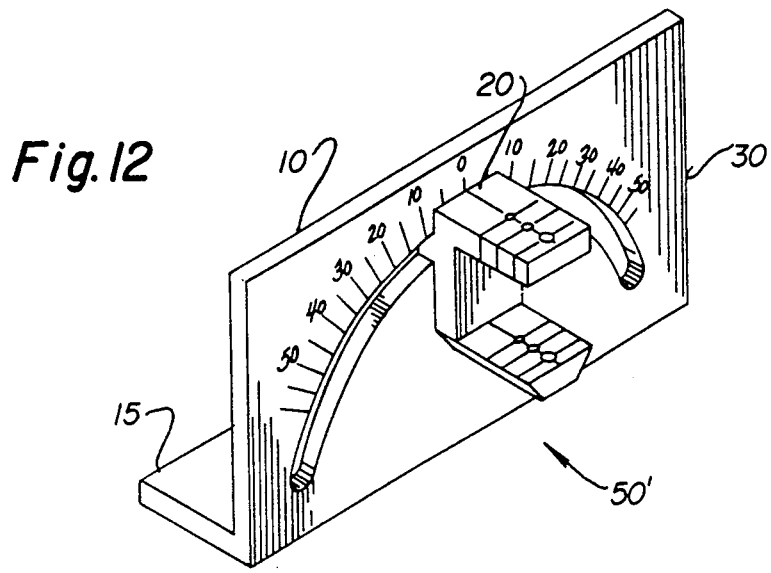
FIG. 12 is a further embodiment of the invention wherein the L-shaped stereotactic device is illustrated in perspective.

In FIG. 1, a preferred embodiment of the invention is shown wherein the stereotactic medical device of the present invention comprising a guidance device 10 is carried, oriented and stabilized by a stereotactic bridge. The stereotactic bridge is comprised of span 100, carried by two stanchions 150, 150'. The bridge is movable horizontally along the length of a C.T. scan table T using a rail guide 160 on which slide 165 supporting linear bearings 130 and 130' is carried. Toggle clamp 166 locks slide 165 in position after horizontal positioning.

Span 100 is movably carried on stanchions 150, 150' by span support members 120, 120'. Vertical positioning of the span is achieved by sliding the span support members up and down the linear bearings of the stanchions 150, 150'. Up and down movement of span 100 is facilitated by use of a negator spring (spring balancer) 145 attached to the span support members by a retractor cord 111.

Positioning side-to-side across the width of the body/table is achieved by moving guidance device 10 which is carried in slot/groove 110 lengthwise along span 100.

A simple means of carriage and affixation in locked position is illustrated in FIG. 2, where thumbscrew 118 is shown in locking engagement with the base 15 of guidance device 10. As best illustrated in FIG. 3, thumbscrew 118 serves the dual purpose of carrier as well as locking means, sliding along slot 110 of span 100.

In FIG. 4, one of the span supports 120 is shown. Toggle clamp 170 is used to lock the span in position on vertical bearing 130'. For this purpose, a more simple arrangement, such as a thumbscrew or other alternatives, is suitable.

Knob 140, which is attached to span 100, is used to rotate the span 100 axially. The mechanism for axial rotation can be chosen from any of the typical arrangements allowing angular adjustment. Thus, for this purpose one may use a mechanism rotatable by means of a knob affixed to a shaft passing through the span support and connected to the bridge.

The specific mechanism and markings for achieving and measuring axial rotation are matters of choice; however, it should be underscored that, in the preferred embodiment of the present invention, where the stereotactic medical device of the present invention is to be used for sagittal introduction, as shown in FIG. 2, the axis of rotation of the span should pivot on a centerline which intersects the point of entry 13 of the medical instrument into the body. This feature is illustrated by reference to the two positions of guidance device 10, A and B, one of which (B) is shown in shadow with the angulation pattern represented by arrow 11. As also shown in FIG. 4, a leveling device, bubble 60, may be used to verify horizontal reference of the stereotactic bridge.

FIG. 5 illustrates a most simple embodiment of the present invention where the guidance device 10 is carried on a span 200 made from a cylindrical rod; and, where cylindrical rods are used for stanchions. As can readily be appreciated, the stability of this simplified embodiment of the invention suffers because of the potential for movement of the stanchion arrangement if care is not exercised by the user.

In FIG. 7, one of the preferred structures of the guidance device (stereotactic device) 10 is shown. The device is T-shaped and comprised of base 15 and leg 30 normal thereto.

Leg 30 has a radial slot 12 therein in which radial portion 22 of carrier 20 rides. Marking 14 along radial slot 12 and marking 22 on carrier 20 are used for radial alignment of the carrier. Apertures 21, 23 and 25 and 21', 23' and 25' are used to retain a needle 98 of syringe 99 along its length in a fixed position on the carrier. Placement of the holes is away from the leg and over the cutout portion indicated generally by numeral 50. This cutout portion likewise denotes generally the sterile field. The stereotactic device illustrated in FIG. 7 has beveled edges 17, 17' and markings 31, 33, 35 for aligning the device on the body.

In FIG. 8, needle 99 is shown in position on carrier 20 with the cannula passing therethrough and after insertion using stereotactic device 10. The position shown in FIG. 8 is that used where a vertical orientation is required. Insertion is illustrated in FIG. 6. A portion of span 200 of the stereotactic bridge is also shown.

Reference to FIGS. 9 to 11, inclusive, illustrates the use of a thumbscrew 24 to lock the carrier 10 in place along slot 12, the threaded portion 26 of thumbscrew 24 being shown in FIG. 9. A thumbscrew 18 lock mechanism from a cylindrical span member is passed through slide member 16 is illustrated in FIG. 9. In FIGS. 10 and 11 an alternative slide member 16' for use with a square-shaped rod 300 and a thumbscrew 18' for locking member 16' onto rod 300 is illustrated. Placement of bubble leveling means 60 on the stereotactic device is illustrated in FIG. 10.

Figure 13:
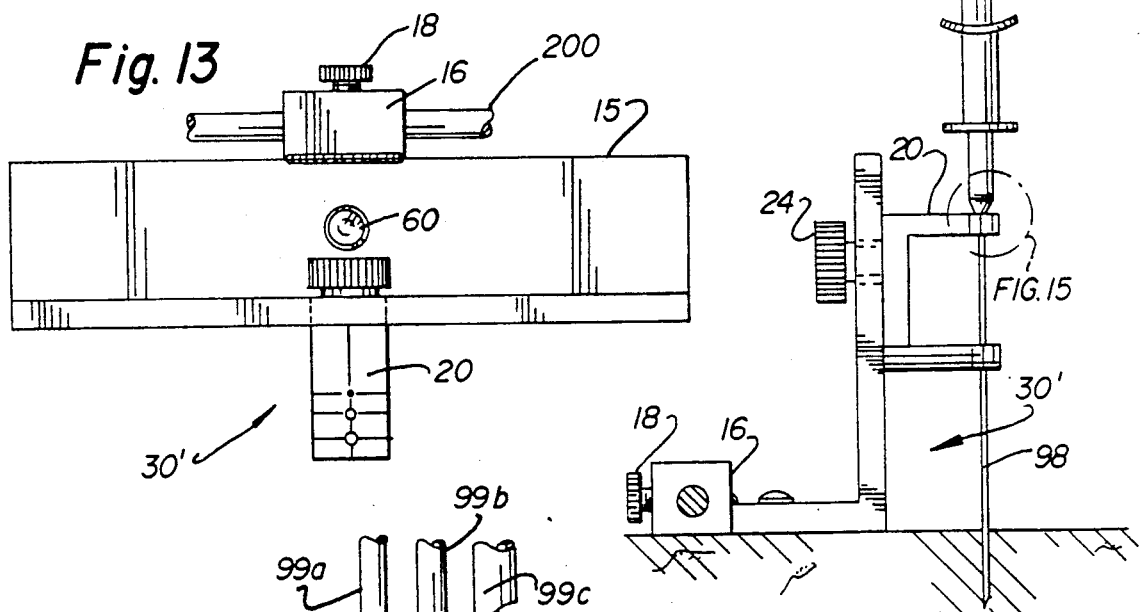
FIG. 13 is a top plan view of FIG. 12 affixed to the span.
Figure 14:
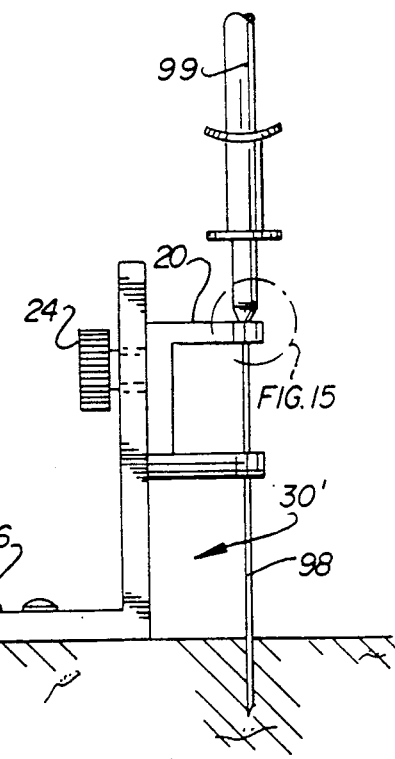
FIG. 14 is an end view of FIG. 12.
Figure 15:
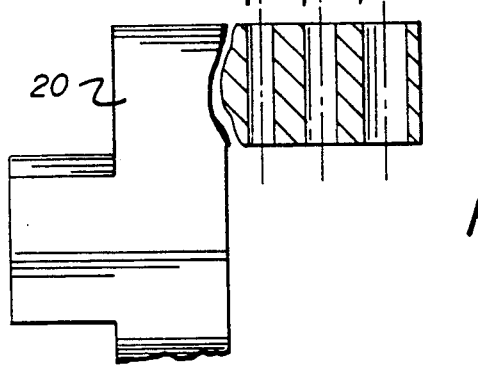
FIG. 15 is a partial view taken from 14 illustrating the use of various sized needles.

FIG. 12 illustrates the L-shaped configuration of guidance device 10 in which the base 15 does not extend (is entirely cutout) on the sterile side of protractor leg 30. This embodiment is particularly suitable for sagittal orientation where any outcropping of the base on the sterile field side of the leg 30 would impede/interfere with axial rotation of the bridge and guidance device. FIGS. 13 through 15 illustrate further, using alternative views, the guidance device 10 of the present invention with FIG. 15 indicating an adaptation of carrier 20 allowing the same carrier to be used for a variety of syringes of differing diameter as shown by reference to needles 99a, 99b and 99c.

DETAILED DESCRIPTION OF THE PREFERRED EMBODIMENT

Use of the Stereotactic Device in C.T. Guided Discectomy (Hand-Held Mode)

A C.T. scan is made of the suspected disc herniation. The patient is placed in the prone position on a scanning table, prepped, and draped in the usual manner.

The point of entrance of the selected site in the skin, as well as the depth and the angle to be used, is calculated under C.T. guidance in a manner well known to the art as follows:

The table top carrying the patient is moved into the gantry and thin 3-5 mm axial tomographic cuts are obtained by C.T. scan through the herniated disc.

The best tomographic cuts is selected and a transverse light beam line identical to the tomographic cut with an X-ray beam is made on the patient and marked on the skin with a colored line.

The point of entrance is marked with a needle and determined by the C.T. scan. The depth and angle are determined by C.T. scan guidance.

Local anesthesia is administered in the skin, muscles, and paravertebral space. A three (3) mm skin incision is made at the selected point of entry of the flex trocar.

Using the stereotactic device for proper guidance of the trocar, the physician inserts the flex trocar slightly posteriorly into the nucleus pulposus of the herniated disc. The stereotactic device is placed on the patient and is oriented so that the trocar is introduced into the body in the plane of the cross-section image developed by the C.T. scanner. This requirement is achieved by aligning the appropriate marking on the stereotactic device (in the plane of trocar travel) with the colored line. The colored line is a reference line drawn on the patient that is within the vertical plane viewed by the C.T. scanner. A marked trocar is used. Such trocars are marked along their length so that the depth of insertion is readily controlled by observing the reference markings and by inserting the same to the predetermined depth by reference to said markings. The proper position of the flex trocar is verified by C.T.

Prior to verification, it is a simple matter, in view of the facile arrangement for disengaging the carrying means, to disengage the carrier and carried medical device from the arcuate slot of the stereotactic device.

A straight cannula with a tapered dilator is passed over the flex trocar and inserted down to the wall of the annulus. The position of the cannula and the position of the flex trocar is again verified by C.T.

Incision is made of the annulus by the trephine, and then the trephine and flex trocar are removed from the cannula.

The nucleotome probe is inserted through the cannula into the nucleus pulposus, and correct position is verified by overhead films on the C.T. scan table.

Suction of the annulus pulposus is performed for approximately 25 minutes, and the patient returns home the same day of the procedure.

Use of The Stereotactic Device In Combination With The Stereotactic Bridge (Stereo-Tactic Bridge Supported Mode)

The patient is placed on the C.T. scan table in the prone position. The lumbar region is prepped and draped in the usual manner.

The table top carrying the patient is moved into the gantry and thin 3-5 mm axial tomographic cuts are obtained by C.T. scan through the herniated disc.

The best tomographic cut is selected and a transverse light beam line identical to the tomographic cut with an X-ray beam is made on the patient and marked on the skin with a colored line.

The point of entrance is marked with a needle and determined by the C.T. scan. The depth and angle are determined by C.T. scan guidance.

The table top carrying the patient is removed from the gantry. The position of the patient on the table top should not be changed in order to maintain the torso in the same position that the torso was in at the time best tomographic cut was taken.

Local anesthesia is administered in the skin, muscles and paravertebral space and a 3 mm in diameter skin incision is made at the selected point of entry of the flex trocar.

The stereotactic bridge is affixed to the C.T. scan table below the movable table top. The bridge can be considered an accessory to the C.T. scan table. The span of the bridge supports and orients the stereotactic device which is situated with the cutout portion circumscribing/delimiting the sterile field over the skin incision. A level on the stereotactic device is used to assure horizontal positioning of the stabilizing table. If a level is on the span, then that level may be checked to verify horizontal positioning. The stereotactic device is aligned and optionally immobilized (locked) on the span. Where the C.T.-generated tomographic cut is made using a sagittal orientation, the span is rotated using a means for measured axial rotation in order to orient the plane of medical device insertion at the exact sagittal orientation of the tomograhic cut.

The flex trocar is inserted with a single pass into the point of interest. The stereotactic device is removed and the patient is moved with the table top of the gantry to the original position. Verification of the position of the flex trocar is made by C.T. scan. It is important for the patient not to move on the table top during the procedure.

A straight cannula with a tapered dilator is passed over the flex trocar and inserted down to the wall of the annulus. The position of the cannula and the position of the flex trocar are again verified by C.T. scan.

Incision of the annulus is made by the trephine, and then the trephine and the flex trocar are removed from the cannula.

The nucleotome probe is inserted through the cannula into the nucleus pulposus and correct position is checked by overhead films on the C.T. scan table.

Suction of the annulus pulposus is performed for approximately 25 minutes, and the patient returns home the same day of the procedure.

In this procedure, it should be noted that verification of positioning can alternatively be made utilizing an X-ray machine appropriately oriented.

Moreover, the stereotactic bridge and stereotactic device combination allows for rapid and precise multiple verification sequences where the procedure is extended and requires repetitive position verification.

Any means of affixation of protractor to bridge may be used. The essential aspect of the invention is that a stereotactic device comprised of a protractor and associated medical device carrier be affixed to a bridge so that, in conjunction, movement orientation and stability required in accordance with the present invention is achieved. Accordingly, the means specified for the function of the stereotactic device, as will be appreciated, can be modified without departing from the invention described and claimed herein.

From the foregoing description it will be apparent that the invention permits simple yet positive orientation of the medical devices described herein. When the proper orientation has been determined, the device may be locked and will then serve to guide the needle or cannula of the desired region of the body. While a preferred embodiment of the invention has been shown and described, it will be apparent to those skilled in the art that changes can be made in this embodiment without departing from the principles and spirit of the invention, the scope of which is defined in the appended claims. Accordingly, the foregoing embodiment is to be considered illustrative, rather than restrictive of the invention, and those modifications which come within the meaning and range of equivalency of the claims are to be included therein.

I claim:

1. A stereotactic device for allowing a user to accurately introduce a medical device through a sterile field into a body at a preselected angle comprising:
   a. a base having an upper surface exposed when the stereotactic device is in use and a lower surface for placement on the body into which the medical device is to be introduced, said base having an opening therein, through which the part of the medical device to be placed within the body can pass unobstructed.
   b. a leg normal to the base, affixed thereto and having a radial slot therein;
   c. a carrier for the medical device comprising:
      i. a radial portion which rides within the radial slot;
      ii. retaining means for retaining the medical device in a fixed radial position relative to the arc defined by the radial slot and downwardly through the opening in the base; and,
      iii. means for locking said carrier at a fixed position on the arcute pathway formed by the slot;
   d. markings on said leg along said radial slot for placement of the retaining means at a preselected point along said radial slot whereby the medical device retained thereby can be extended downwardly through the opening and into the body at a preselected angle; and
   e. markings on the base of said device for orienting said base, said base having opposing edges contiguous with the upper surface thereof and normal to the leg which edges are beveled and slope downwardly and outward from the surface of the base, said markings on said base comprising markings on said beveled edges.

2. The stereotactic device of claim 1, wherein the device is T-shaped and the leg of said device divides said base into a first part delimiting the sterile field and a second part remote from the sterile field and separated therefrom by said leg, said stereotactic device further characterized in that there are markings on the base of said device for orientation of said base on the body.

3. The stereotactic device of claim 2, wherein a leveling means is associated with the device to assist in orienting the longitudinal axis of the base horizontally.

4. The stereotactic device of claim 3, wherein the leveling means is a circular bubble level on the upper surface of the base.

5. The stereostatic device of claim 1, wherein the angle of the bevel, at the opposing edges, is from about 15° to about 75°.

6. The stereotactic device of claim 1, wherein the base is made of a transparent material, the markingse are on the upper surface of said base and the markings run along at least a portion of the length of the upper surface of the base in parallel with the leg.

.7. A stereotactic medical device for accurate placement of a medical instrument through a sterile field into a body at a preselected angle in a plane of horizontal or sagittal orientation comprising:
   a. a stereotactic bridge comprising:

(i) a span;
(ii) stanchions supporting said span;
(iii) means for moving said span vertically up and down said stanchions;
(iv) means for moving said stanchions horizontally;
(v) means for axially rotating the span in correlation with the angulation of a C.T. scanner to enable sagittal insertion of the medical device;

b. a guidance device for accurate introduction of a part of a medical device of a given length into said body, said device comprising:
(i) a base comprised of a plate and an upstanding leg positioned substantially perpendicular to the plate, said plate on one side of said upstanding leg having a cutout opening delimiting the sterile field through which a lower part of the medical device can pass unobstructed to a predetermined position and on the other side of said upstanding leg, said plate having a means for connecting said guidance device to said span of said stereotactic bridge, said leg comprised of an arcuate track with means therealong for indicating a plurality of preselected angles relative to the predetermined position which is accessible through the opening in the plate; and
(ii) a carrier including means for movement along the arcuate track, means for retaining the medical device in a fixed position relative to the riding means, and means for locking the retaining means at one of the preselected angles relative to the predetermined position;

whereby the lower part of the medical device-retained by the carrier can be extended through the opening in the plate and into the predetermined position at said one of the preselected angles;

c. means for moving and locking the guidance device defined in "b" along the length of said span, said means including said means for connecting said guidance device to said span of said stereotactic bridge; and d. means for leveling the guidance device after the guidance device is connected to the span.

8. The medical device of claim 7, wherein said leveling means is a leveling bubble on the guidance device on the span.

9. The medical device of claim 8, wherein the axis of rotation of the span pivots on a centerline which intersects the point of entry of the medical device into the body.

10. The medical device of claim 7, wherein the arcuate track is an arcuate slot of a given width cut through said leg and the means for movement along the arcuate track comprises a means for riding within the arcuate slot cut through the leg.

11. The medical device of claim 10, wherein the axis of rotation of the span pivots on a centerline which intersects the point of entry of the medical device into the body.

12. The medical device of claim 7, wherein the axis of rotation of the span pivots on a centerline which intersects the point of entry of the medical device into the body.

13. The medical device of claim 7, wherein the axis of rotation of the span pivots on a centerline which intersects the point of entry of the medical device into the body.

14. A stereotatic medical device for accurate placement of a medical instrument through a sterile field into a body at a preselected angle in a plane of horizontal or sagittal orientation comprising:

a. a stereotactic bridge comprising:
(i) a span;
(ii) stanchions supporting said span;
(iii) means for moving said span vertically up and down said stanchions, said means for moving said span vertically up and down including a negator spring for facilitating said vertical up and down movement;
(iv) means for moving said stanchions horizontally;
(v) means for axially rotating the span in correlation with th angulation of a C.T. scanner to enable sagittal insertion of the medical device;

b. a guidance device for accurate introduction of a part of a medical device of a given length into said body, said device comprising:
(i) a base comprised of a plate and an upstanding leg positioned substantially perpendicular to the plate, said plate on one side of said upstanding leg having a cutout opening delimiting the sterile field through which a lower part of the medical service can pass unobstructed to a predetermined position and on the other side of said upstanding leg, said plate having a means for connecting said guidance device to said span of said stereotactic bridge, said leg comprised of an arcuate track with means therealong for indicating a pluarlity of preselected angles relative to the predetermined position which is accessible through the opening in the plate; and
(ii) a carrier including means for movement along the arcuate track, means for retaining the medical device in a fixed position relative to the riding means, and means for locking the retaining means at one of the preselected angles relative to the predetermined position;

whereby the lower part of the medical device retained by the carrier can be extended through the opening in the plate and into the predetermined position at said one of the preselected angles; and c. means for moving and locking the guidance device defined in "b" along the length of said span, said means including said means for connecting said guidance device to said span of said stereotactic bridge.

15. A stereotactic medical device for accurate placement of a medical instrument through a sterile field into a body at a preselected angle in a plane of horizontal or sagittal orientation comprising:

a. a stereotactic bridge comprising:
(i) a span;
(ii) stanchions supporting said span;
(iii) means for moving said span vertically up and down said stanchions;
(iv) means for moving said stanchions horizontally;
(v) means for axially rotating the span in correlation with the angulation of a C.T. scanner to enable sagittal insertion of the medical device;

b. a guidance device for accurate introduction of a part of a medical device of a given length into said body, said device comprising:
(i) a base comprised of a plate and an upstanding leg positioned substantially perpendicular to the plate, said plate on one side of said upstanding leg having a cutout opening delimiting the sterile field through which a lower part of the medical device can pass unobstructed to a predetermined position and on the other side of said upstanding leg, said plate having a means for connecting said guidance device to said span of said stereotactic bridge, said leg comprised of an arcuate track with means therealong for indicating a plurality of preselected angles relative to the predetermined position which is accessible through the opening in the plate; and (ii) a carrier including means for movement along the arcuate track, means for retaining the medical device in a fixed position relative to the riding means, said retaining means comprising a pair of arms with threaded bores therethrough and spaced from each other at a distance less than the given length of the medical device so that said medical device can be held securely in the bores thereof, and means for locking the retaining means at one of the preselected angles relative to the predetermined position;

whereby the lower part of the medical device retained by the carrier can be extended through the opening in the plate and into the predetermined position at said one of the preselected angles;

c. means for moving and locking the guidance device defined in "b" along the length of said span, said means including said means for connecting said guidance device to said span of said stereotactic bridge.

16. The medical device of claim 15, wherein the locking means of the guidance device includes a threaded fastener means for engaging the threaded bore through the cylindrical protrusion of the riding means.

17. The medical device of claim 16, wherein the axis of rotation of the span pivots on a centerline which intersects the point of entry of the medical device into the body.

* * * * *